(12) United States Patent
Maleki et al.

(10) Patent No.: US 8,907,684 B2
(45) Date of Patent: Dec. 9, 2014

(54) NANOFLUIDIC CHANNEL WITH EMBEDDED TRANSVERSE NANOELECTRODES AND METHOD OF FABRICATION FOR SAME

(75) Inventors: Teimour Maleki, West Lafayette, IN (US); Babak Ziaie, West Lafayette, IN (US); Saeed Mohammadi, Zionsville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 568 days.

(21) Appl. No.: 13/143,086

(22) PCT Filed: Jan. 29, 2010

(86) PCT No.: PCT/US2010/022568
§ 371 (c)(1),
(2), (4) Date: Aug. 14, 2011

(87) PCT Pub. No.: WO2010/088506
PCT Pub. Date: Aug. 5, 2010

(65) Prior Publication Data
US 2011/0285409 A1 Nov. 24, 2011

Related U.S. Application Data

(60) Provisional application No. 61/148,948, filed on Jan. 31, 2009.

(51) Int. Cl.
*G01R 27/26* (2006.01)
*G01N 33/487* (2006.01)

(52) U.S. Cl.
CPC .............................. *G01N 33/48721* (2013.01)

USPC ............................ 324/679; 257/207; 257/787

(58) Field of Classification Search
CPC ... C12Q 2563/157; B82Y 30/00; B82Y 15/00
USPC ......... 324/679, 606, 649, 658, 665, 672, 705; 257/207, 787
See application file for complete search history.

(56) References Cited

U.S. PATENT DOCUMENTS 5,681,484 A * 10/1997 Zanzucchi et al. .............. 506/40
6,503,409 B1 * 1/2003 Fleming .......................... 216/56

(Continued)

OTHER PUBLICATIONS

Margaret B. Stern, Michael W. Geis, and Jane E. Curtin, "Nanochannel fabrication for chemical sensors," Journal of Vacuum Science & Technology B, 1997, vol. 15(6) Nov/Dec, pp. 2887-2891.

(Continued)

*Primary Examiner* — Tung X Nguyen
*Assistant Examiner* — Giovanni Astacio-Oquendo
(74) *Attorney, Agent, or Firm* — Purdue Research Foundation

(57) ABSTRACT

A method for forming a nanofluidic channel measuring system is disclosed. The method includes forming a first trench in a substrate, forming a second trench in the substrate, the first trench and the second trench are separated by a first width, providing a first conductor pad at a first location, providing a second conductor pad at a second location, forming a first nano-wire for coupling the first conductor pad with the second conductor pad, and forming a nano-channel through the first nano-wire, the nano-channel also coupling the first trench and the second trench, the nano-channel configured to sever the first nano-wire. A nanofluidic channel measuring system is also disclosed.

18 Claims, 12 Drawing Sheets

(56) References Cited

U.S. PATENT DOCUMENTS

| | | | |
|---|---|---|---|
| 6,593,065 B2* | 7/2003 | Scherer | 430/314 |
| 6,815,688 B2* | 11/2004 | Schneiker et al. | 250/396 R |
| 7,037,400 B1* | 5/2006 | Shaw et al. | 156/268 |
| 7,678,562 B2* | 3/2010 | Ling | 435/283.1 |
| 2003/0209314 A1* | 11/2003 | Guo et al. | 156/247 |
| 2007/0238112 A1* | 10/2007 | Sohn et al. | 435/6 |
| 2008/0150154 A1* | 6/2008 | Hedler et al. | 257/776 |
| 2009/0047681 A1* | 2/2009 | Han et al. | 435/6 |
| 2009/0214392 A1* | 8/2009 | Kameoka et al. | 422/102 |

OTHER PUBLICATIONS

S. Gawad, L. Schild, and Ph. Renaud, "Micromachined impedance spectroscopy flow cytometer for cell analysis and particle sizing," Lab on a Chip, 2001, vol. 1, pp. 76-82.

Derek Stein, Frank H.J. van der Heyden, Wiepke J. A. Koopmans, and Cees Dekker, "Pressure-driven transport of confined DNA polymers in fluidic channels," PNAS Oct. 24, 2006, vol. 103, No. 43, pp. 15853-15858.

Christian H. Reccius, Samuel M. Stavis, John T. Mannion, Larry P. Walker, and H. G. Craighead, "Conformation, length, and speed measurements of electrodynamically stretched DNA in nanochannels," Biophysical Journal, Jul. 2008, vol. 95, pp. 273-286.

Walter Reisner, Keith J. Morton, Robert Riehn, Yan Mei Wang, Zhaoning Yu, Michael Rosen, James C. Sturm, Stephen Y. Chou, Erwin Frey, and Robert H. Austin, "Statics and dynamics of single DNA molecules confined in nanochannels," Physical Review Letters, May 20, 2005, vol. 94, pp. 196101-1-196101-4.

Sumita Pennathur and Juan G. Santiago, "Electrokinetic transport in nanochannels. 2. Experiments," Analytical Chemistry, 2005, vol. 77, pp. 6782-6789.

R. Qiao and N. R. Aluru, "Charge inversion and flow reversal in a nanochannel electro-osmotic flow," Physical Review Letters, May 14, 2004, vol. 92, No. 19, pp. 198301-1-198301-4.

Hangjun Lu, Jingyuan Li, Xiaojing Gong, Rongzheng Wan, Li Zeng, and Haiping Fang, "Water permeation and wavelike density distributions inside narrow nanochannels," Physical Review B, 2008, vol. 77, 174115-1-174115-8.

Michael Zwolak and Massimiliano Di Ventra, "Physical approaches to DNA sequencing and detection," Reviews of Modern Physics, Jan.-Mar. 2009, vol. 80, pp. 141-165.

Ken Healy, "Nanopore-based single-molecule DNA analysis," Nanomedicine, 2007, vol. 2(4), pp. 459-481.

Aleksij Aksimentiev, Jiunn B. Heng, Gregory Timp, and Klaus Schulten, "Microscopic kinetics of DNA translocation through synthetic nanopores," Biophysical Journal, Sep. 2004, vol. 87, pp. 2086-2097.

N. R. Tas, J. W. Berenschot, P. Mela, H V. Jansen, M. Elwenspoek, and A. van den Berg, "2D-confined nanochannels fabricated by conventional micromachining," Nano Letters, 2002, vol. 2, No. 9, pp. 1031-1032.

J. B. Heng, A. Aksimentiev, C. Ho, P. Marks, Y. V. Grinkova, S. Sligar, K. Schulten, and G. Timp, "The electromechanics of DNA in a synthetic nanopore," Biophysical Journal, Feb. 2006, vol. 90, pp. 1098-1106.

Vincent Tabard-Cossa, Dhruti Trivedi, Matthew Wiggin, Nahid N. Jetha, and Andre Marziali, "Noise analysis and reduction in solid-state nanopores," Nanotechnology, 2007, vol. 18, pp. 305505-1-305505-6.

Jeroen Haneveld, Henri Jansen, Erwin Berenschot, Niels Tas, and Miko Elwenspoek, "Wet anisotropic etching for fluidic 1D nanochannels," Journal of Micromechanics and Microengineering, 2003, vol. 13, pp. S62-S66.

Pan Mao and Jongyoon Han, "Fabrication and characterization of 20 nm planar nanofluidic channels by glass-glass and glass-silicon bonding," Lap on a Chip, 2005, vol. 5, pp. 837-844.

Changju Wu, Zhonghe Jin, HuiQuan Wang, Huilian Ma, and Yuelin Wang, "Design and fabrication of a nanofluidic channel by selective thermal oxidation and etching back of silicon dioxide made on a silicon substrate," Journal of Micromechanics and Microengineering, 2007, vol. 17, pp. 2393-2397.

Choonsup Lee, Eui-Hyeok, (E. H.) Yang, Nosang V. Myung, and Thomas George, "A nanochannel fabrication technique without nanolithography," Nano Letters, 2003, vol. 3, No. 10, 1339-1340.

Han Cao, Zhaoning Yu, Jian Wang, Jonas O. Tegenfeldt, Robert H. Austin, Erli Chen, Wei Wu, and Stephen Y. Chou, "Fabrication of 10 nm enclosed nanofluidic channels," Applied Physics Letters, Jul. 1, 2002, vol. 81, No. 1, pp. 174-176.

J. P. Alarie, A. B. Hmelo, S. C. Jacobson, A. P. Baddorf, L. Feldman, and J. M. Ramsey, "Fabrication and evaluation of 2D confined nanochannels," m-TAS 2003, vol. 1, pp. 9-12.

Rohit Karnik, Rong Fan, Min Yue, Deyu Li, Peidong Yang, and Arun Majumdar, "Electrostatic control of ions and molecules in nanofluidic transistors," Nano Letters, 2005, vol. 5. No. 5, pp. 943-948.

R. Rodriguez-Trujillo, C. A. Mills, J. Samitier, and G. Gomila, "Low cost micro-Coulter counter with hydrodynamic focusing," Microfluid Nanofluid, 2007, vol. 3, pp. 171-176.

T. Maleki, S. Mohammadi, and B. Ziaie, "A nanofluidic channel with embedded transverse nanoelectrodes," Nanotechnology, 2009, vol. 20, 105302-1-105302-6.

Youngkyun Jung, "Velocity inversion in nanochannel flow," Physical Review E, 2007, vol. 75, 051203-1-051203-5.

\* cited by examiner

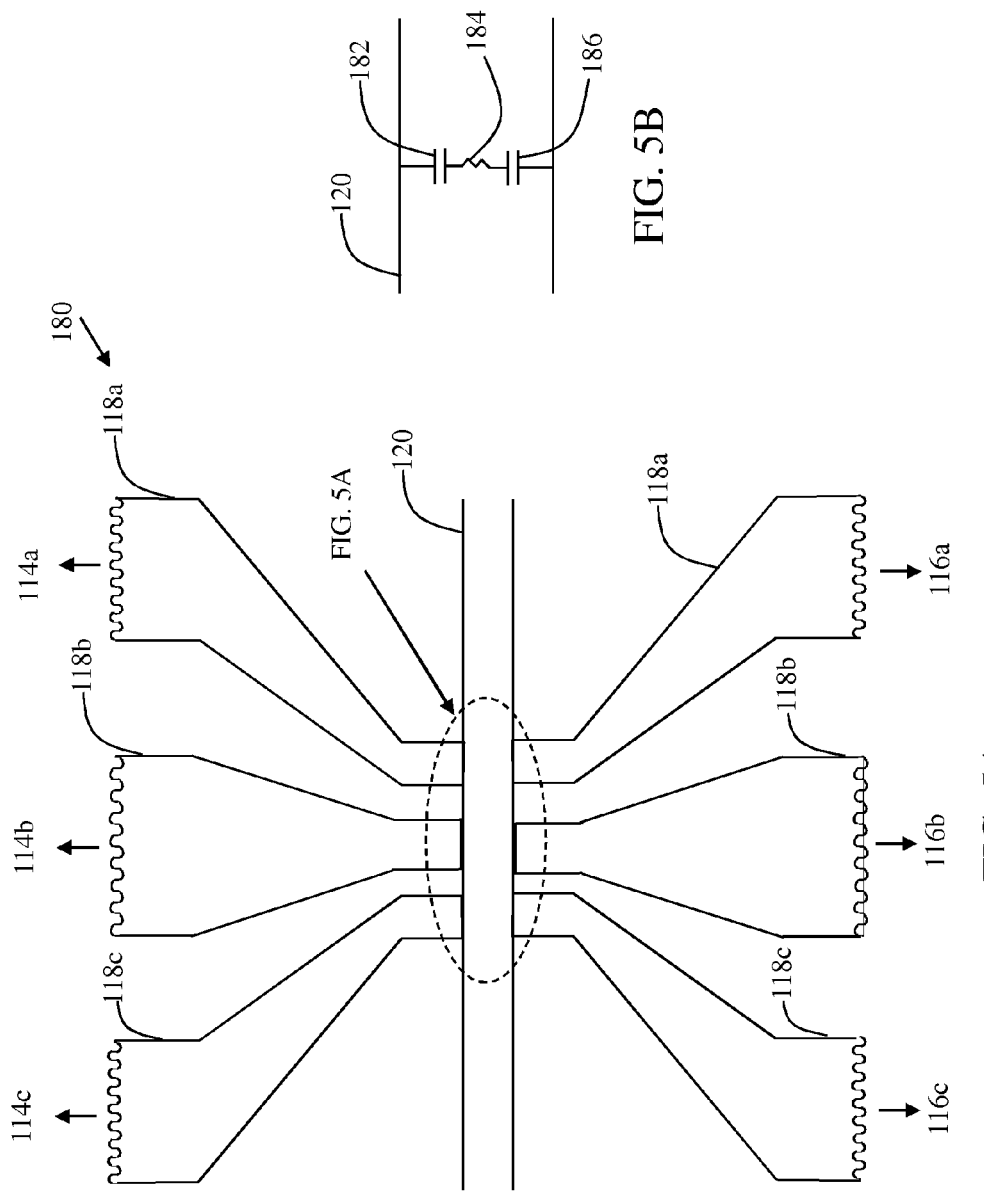

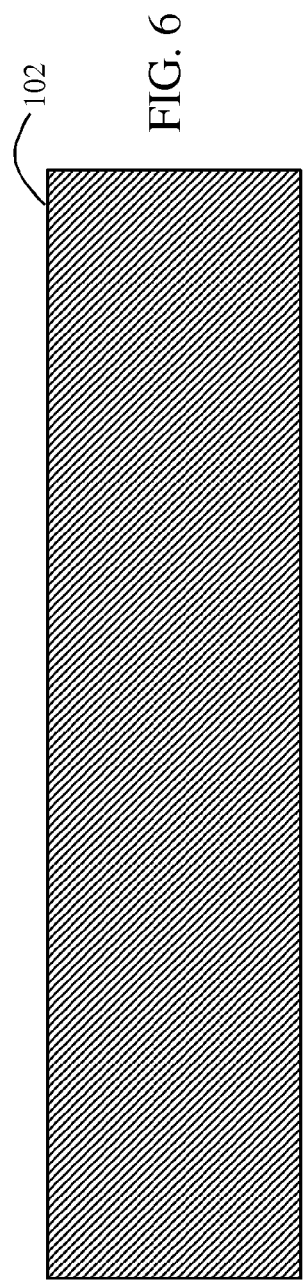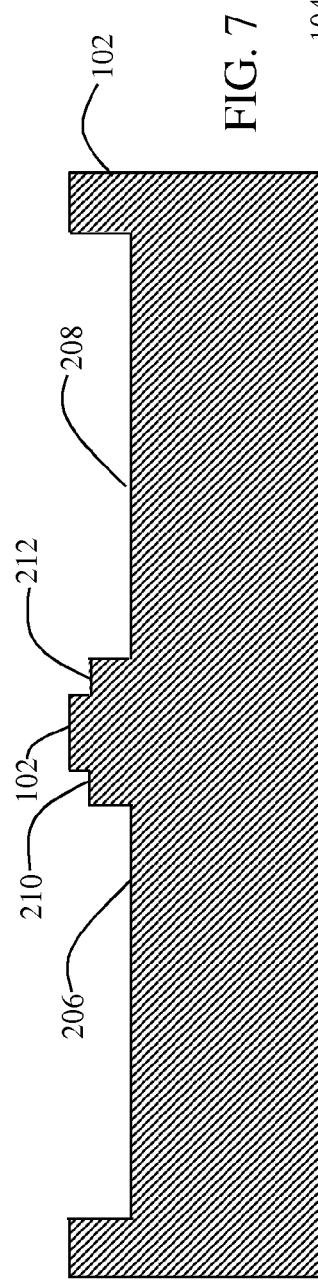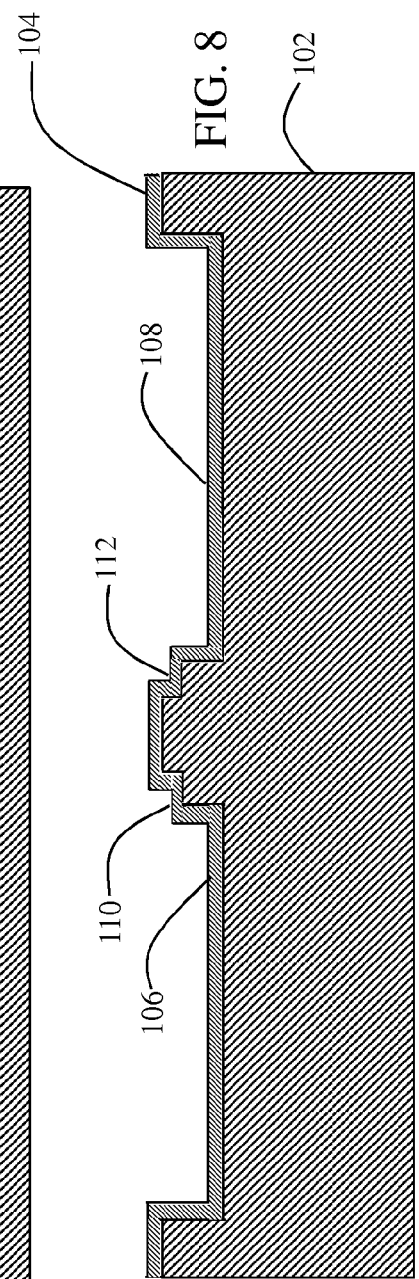

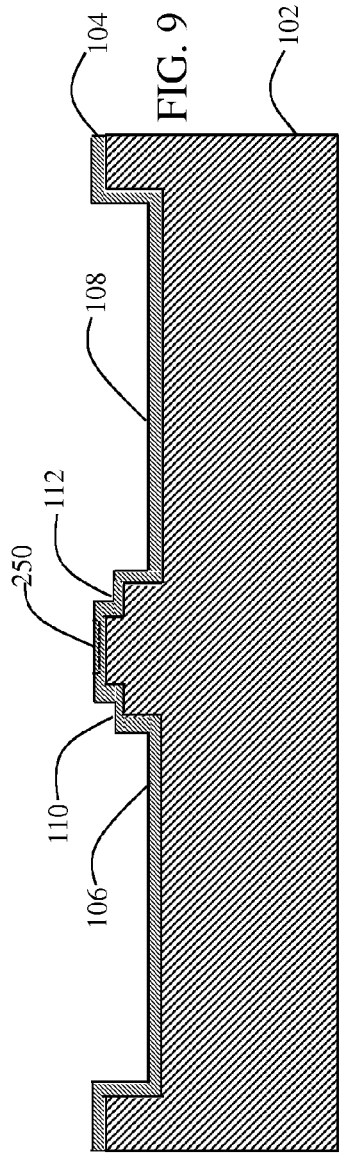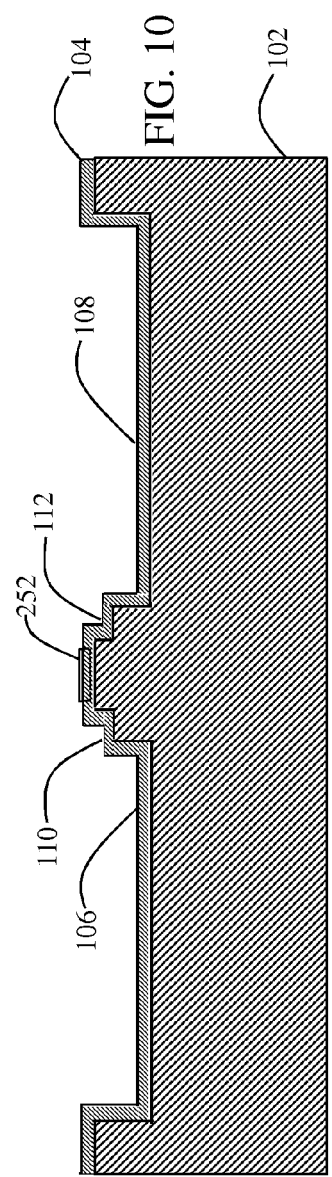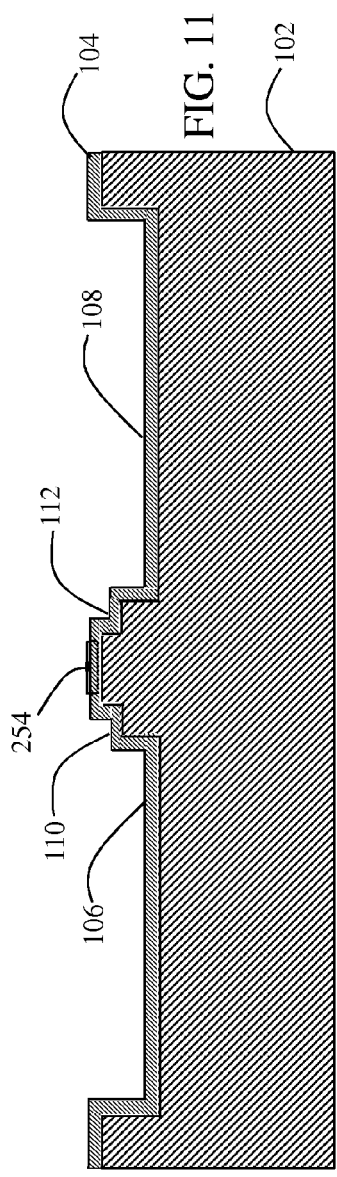

NANOFLUIDIC CHANNEL WITH EMBEDDED TRANSVERSE NANOELECTRODES AND METHOD OF FABRICATION FOR SAME

PRIORITY

The present application is related to, claims the priority benefit of, and is a U.S. §371 national stage entry of, International Patent Application Serial No. PCT/US2010/022568, filed Jan. 29, 2010, which is related to, and claims the priority benefit of U.S. Provisional Patent Application Ser. No. 61/148,948, filed Jan. 31, 2009. The contents of each of these applications are hereby incorporated by reference in their entirety into this disclosure.

TECHNICAL FIELD

The present invention generally relates to nano-size conduits and particularly to a nanofluidic channels with nano-electrodes.

BACKGROUND

In recent years technologies directed to sensing presence of particles in a channel have made significant advances. One such technology is a Coulter counter, designed and developed by Wallace H Coulter in 1947. The Coulter counter is used for counting and sizing particles and cells. The theory behind a Coulter counter is that there is a change in electrical conductance of an electrically conducting liquid flowing through the channel when a small non-conducting particle passes through the channel. Cells can be modeled as spheres with a non-conducting outer shell, i.e., the cell membrane. As will be discussed below, the coulter counter can detect cells in the channel, thereby allowing the cells to be identified and counted.

The Coulter counter operates by measuring the electrical resistance of a channel. When the channel is dry, the electrical resistance is high, i.e., an open circuit. When an electrically conducting liquid fills the channel, the electrical resistance drops significantly. However, when a cell, with a non-conducting outer membrane, passes through the channel that is filled with the conducting liquid, the cell displaces the liquid. The displacement of the conducting liquid with the cell having a non-conducting membrane results in an increase in the resistance of the channel. The increase in the resistance can be correlated to the size of the cells and the number of the cells.

Today, the Coulter counter is the core of many laboratory equipment used in hospital laboratories. For example, a complete blood count testing machine is used for counting the cells and determining the size of other particles present in a blood sample in an automated manner. The complete blood count testing machine can provide its results in minutes. The function of the complete blood count testing was traditionally performed manually by laboratory technicians. The manual process involved preparing a blood cell stain and manually counting each type of cell under a microscope. This type of manual counting is time consuming and prone to variation from technician to technician.

While Coulter counters have replaced manual counting of blood cell constituents, counters capable of effectively counting smaller nano-sized particles, i.e., particles with sizes in the nano-meter range, i.e., $10^{-9}$ m, are only now becoming available. Many of these new systems use expensive and sophisticated equipment. For example, a line of nano-size particle identification technologies are based on imaging light that scatters from the particles. The light scattering technology may use an electron multiplication charge coupled device camera system for improving sensitivity. In addition to expense, these systems have limited capabilities. In particular, the lower limit for particle size may be 10 nm.

In addition to counting nano-sized particles, recent developments in Deoxyribonucleic acid molecule (DNA) sequencing and Ribonucleic acid molecule (RNA) sequencing have generated a need for manipulating DNA and RNA molecules. The DNA and RNA molecules are made of strands with feature sizes as small as 1-2 nm. As a result, a DNA/RNA molecule manipulator must be sensitive to the single-digit nm sized features of the DNA/RNA strands.

Therefore, there is a need for both a counter that can count single nano-meter sized particles and further control and manipulate these particles.

SUMMARY

A method for forming a nanofluidic channel measuring system is disclosed. The method includes forming a first trench in a substrate, forming a second trench in the substrate, the first trench and the second trench are separated by a first width, providing a first conductor pad at a first location, providing a second conductor pad at a second location, forming a first nano-wire for coupling the first conductor pad with the second conductor pad, and forming a nano-channel through the first nano-wire, the nano-channel also coupling the first trench and the second trench, the nano-channel configured to sever the first nano-wire.

The first nano-wire of the method extends over the first width.

The nano-channel of the method extends along the first width.

The nano-wire of the method is substantially perpendicular to the nano-channel.

The method further includes providing a thermal oxide layer over the substrate prior to providing the first conductor pad and the second conductor pad, forming a first recess at the first location where the first conductor pad is to be provided, and forming a second recess at the second location where the second conductor pad is to be provided, wherein the first conductor pad is provided inside the first recess and the second conductor pad is provided inside the second recess.

The first conductor pad and the second conductor pad of the method are thicker than depths of the first recess and the second recess.

The first trench and the second trench of the method are formed by deep reactive ion etching, and the first nano-wire is formed by a first focus ion beam process.

The nano-channel of the method is formed by a second focused ion beam process.

The nano-channel of the method is formed by an atomic force microscope.

The method further includes forming a first shallow trench between the first width and the first reservoir, and forming a second shallow trench between the first width and the second reservoir.

The first shallow trench and the second shallow trench of the method are formed by a deep reactive ion etching process.

The method further includes forming a layer to be placed over the substrate, forming access holes to provide access to the first trench and the second trench, forming access holes to provide access to the first conductor pad and to the second conductor pad, and bonding the layer over the substrate.

The method further includes providing a third conductor pad prior to forming the nano-channel, forming a second nano-wire between the first conductor pad and the third conductor pad prior to forming the nano-channel, wherein the nano-channel severs the second nano-wire, and the nano-channel is substantially perpendicular to the second nano-wire.

The method further includes applying a microwave stimulus to the first conductor pad, measuring conductance across the nano-channel by sensing a response at the second conductor pad, and measuring reflectance of the microwave stimulus by sensing a response at the first conductor pad.

The method further includes storing command instructions in a memory, and configuring a processor to execute the command instructions to energize the first conductor pad, measure voltage at the second conductor pad, and provide an output associated with electrical characteristics between the first conductor pad and the second conductor pad, wherein the electrical characteristics include impedance between the first conductor pad and the second conductor pad, and admittance between the first conductor pad and the second conductor pad.

A nanofluidic channel measuring system is also disclosed. The nanofluidic channel measuring system includes a substrate having a first trench formed therein and a second trench formed therein, the first trench and the second trench are separated by a first width, a first conductor pad disposed at a first location, a second conductor disposed at a second location, a nano-channel configured to couple the first trench and the second trench along a first width, a first nano-wire section extending form the first conductor pad to the nano-channel, and a second nano-wire section extending from the second conductor pad to the nano-channel.

The nanofluidic channel measuring system further includes a thermal oxide layer disposed over the substrate, wherein the thermal oxide layer is disposed between the substrate and the first conductor pad and between the substrate and the second conductor pad, a first recess having a first depth in the thermal oxide disposed at the first location under the first conductor pad, and a second recess having a second depth in the thermal oxide disposed at the second location under the second conductor pad.

The first conductor pad of the nanofluidic channel measuring system is thicker than the first depth of the first recess and the second conductor pad is thicker than the second depth of the second recess.

The nanofluidic channel measuring system further includes a first shallow trench disposed between the first width and the first reservoir, and a second shallow trench disposed between the first width and the second reservoir.

The nanofluidic channel measuring system further includes a layer disposed over the substrate, access holes disposed in the layer to provide access to the first trench and the second trench, and access holes disposed in the layer to provide access to the first conductor pad and to the second conductor pad.

The nanofluidic channel measuring system further includes a third conductor pad disposed at a third location, and a third nano-wire section extending from the third conductor pad to the nano-channel.

The nanofluidic channel measuring system of further includes a memory for storing command instructions, and a processor configured to execute the command instructions to energize the first conductor pad, measure voltage at the second conductor pad, and provide an output associated with electrical characteristics between the first conductor pad and the second conductor pad, wherein the electrical characteristics include impedance between the first conductor pad and the second conductor pad, and capacitance between the first conductor pad and the second conductor pad.

The described features and advantages, as well as others, will become more readily apparent to those of ordinary skill in the art by reference to the following description and accompanying drawings.

BRIEF DESCRIPTION OF DRAWINGS

FIG. 5A depicts a fragmentary plan view of an set of electrode wires used for providing microwave stimuli and for measuring electrical characteristics of a medium in a nano-channel of the nano-channel sensor of FIG. 2;

FIG. 5B depicts an electrical model of the nano-channel of FIG. 5A;

FIGS. 6 through 11 depict steps for fabricating the nano-channel sensor depicted in FIG. 2;

DETAILED DESCRIPTION

Figure 1:
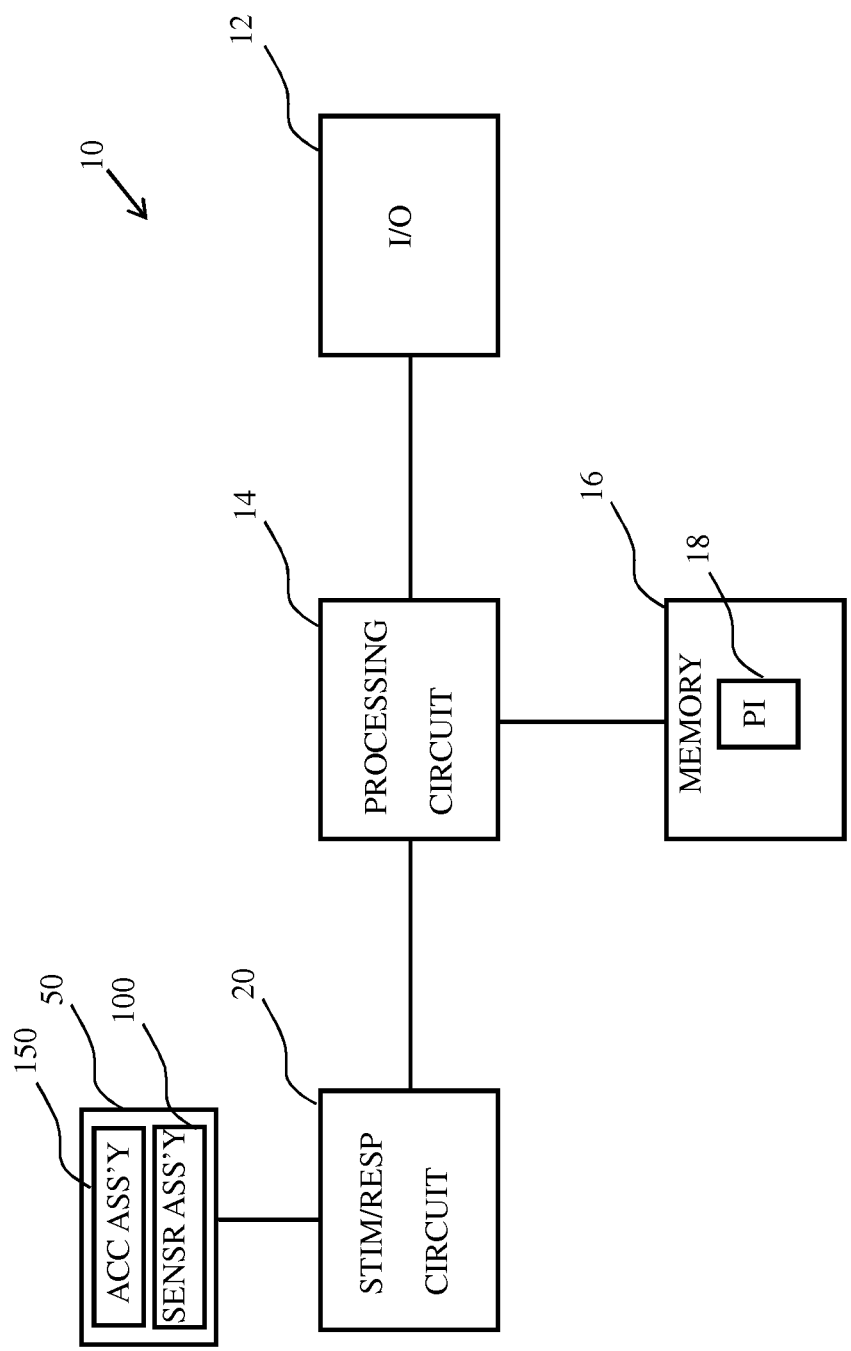
FIG. 1 depicts a block diagram of a nano-channel measuring system including a nano-channel sensor assembly.

FIG. 1 depicts a nano-channel measuring system 10. The nano-channel measuring system 10 includes an I/O device 12, a processing circuit 14 and a memory 16. The I/O device 12 may include a user interface, graphical user interface, keyboards, pointing devices, remote and/or local communication links, displays, and other devices that allow externally generated information to be provided to the nano-channel measuring system 10, and that allow internal information of the nano-channel measuring system 10 to be communicated externally.

The processing circuit 14 may suitably be a general purpose computer processing circuit such as a microprocessor and its associated circuitry. The processing circuit 14 is operable to carry out the operations attributed to it herein.

The memory 16 stores program instructions 18 that are executed by the processing circuit 14 and/or any other components as appropriate.

The nano-channel measuring system 10 further includes a sensor stimulus/response circuit 20 connected to the processing circuit 14. The sensor stimulus/response circuit 20 provides a stimulus for a nano-channel sensor assembly 50 and measures the effects of the stimulus. The stimulus may be controlled by the processing circuit 14 and the measured value is communicated to the processing circuit 14. The nanochannel sensor assembly 50 includes a nano-channel sensor 100 and an access cover assembly 150.

Figure 2:
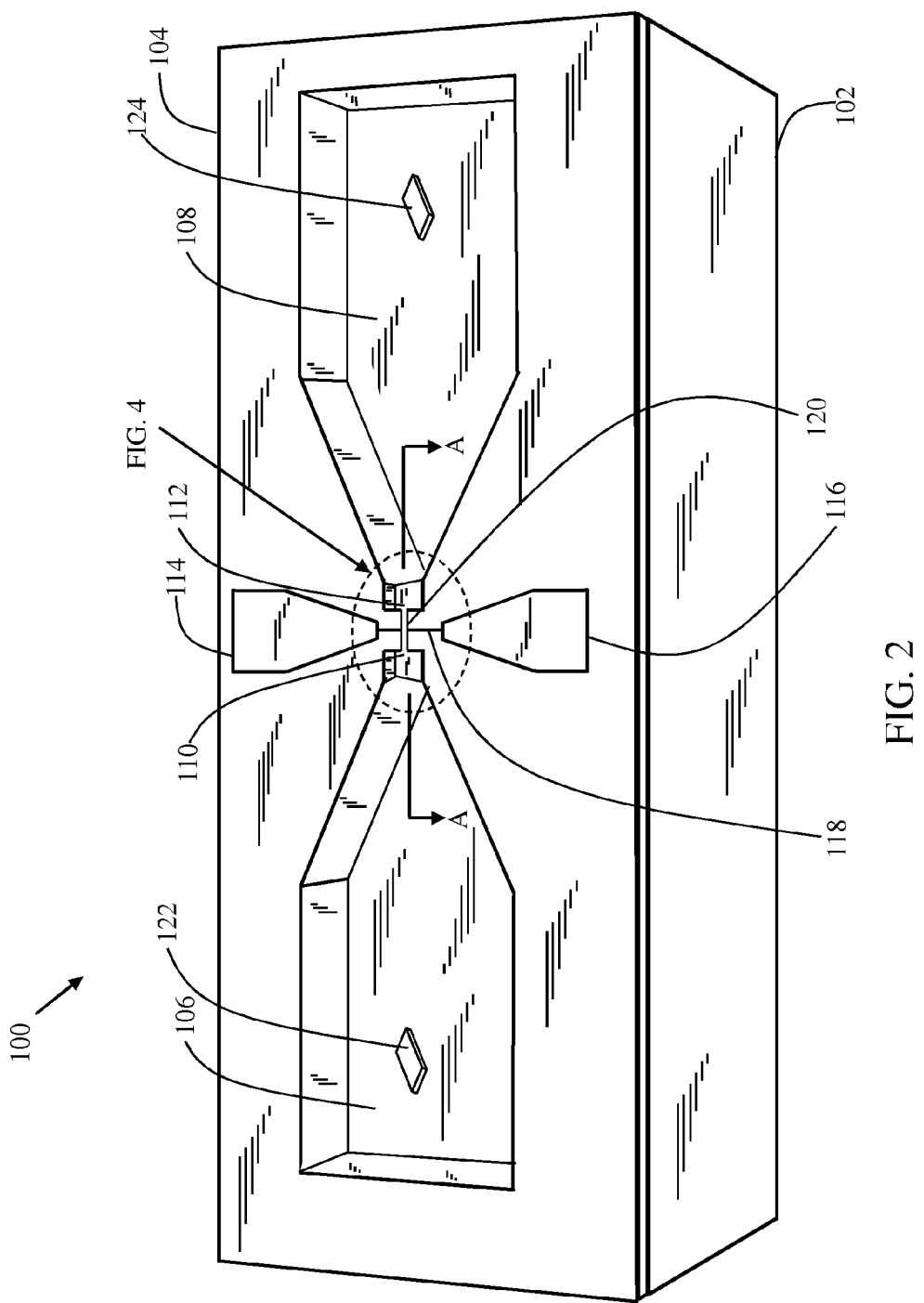
FIG. 2 depicts a perspective view of a nano-channel sensor of the nano-channel sensor assembly of FIG. 1.

FIG. 2 depicts a perspective view of the nano-channel sensor 100. The nano-channel 100 includes a substrate 102, a thermal oxide layer 104, reservoirs 106 and 108, micro-channels 110 and 112, conductor pads 114 and 116, electrode wire 118, a nano-channel 120, and biasing terminals 122 and 124. The thermal oxide layer 104 is an oxide layer that provides thermal and electrical isolation that is known in the art. The thermal oxide layer 104 is disposed over the substrate 102. The conductor pads 114 and 116, and the electrode wire 118 are formed over the thermal oxide layer 104. The nano-channel 120 is formed inside the thermal oxide layer 104. By contrast, the reservoirs 106 and 108 are formed in the substrate prior to formation of the thermal oxide layer 104. The reservoirs 106 and 108 are substantially deeper structures than the micro-channels 110 and 112. The biasing terminals 122 and 124 are disposed in the reservoirs 106 and 108. While a single reference numeral 118 is provided for the electrode wire, it should be appreciated that the electrode wire 118 is in two sections, i.e., a first section and a second section. The first section extends between the conductor pad 114 and the nano-channel 120. The second section extends between the conductor pad 116 and the nano-channel 120.

In the exemplary embodiment depicted in FIG. 2, the reservoirs 106 and 108 are about 150 μm deep, the micro-channels 110 and 112 are about 1 μm deep, and the thermal oxide layer 104 is about 7000 Å, i.e., 0.7 μm thick. Also, in the exemplary embodiment depicted in FIG. 2, the conductor pads 114 and 116 are about 110 nm thick, made of a 10 nm chromium bottom layer and a 100 nm gold top layer, while the electrode wire 118 is between 1 and 10 nm thick and made of platinum. The biasing terminals 122 and 124 have similar construction details as the conductor pads 114 and 116. The nano-channel 120 is a recess in the thermal oxide layer 104 with a depth of about 1 nm to 100 nm. The equipment that forms the nano-channel, discussed below, also cuts the electrode wire 118, forming an electrical open circuit about the nano-channel 120. The length of the nano-channel 120 is inversely proportional to the rate of flow that a liquid can travel through it. Therefore, a longer nano-channel 120 can result in a slower transfer of the liquid.

The electrode wire 118 is connected to the conductor pads 114 and 116. The reservoir 106 is adjacent and can be in fluid communication with the micro-channel 110. The reservoir 108 is adjacent and is in fluid communication with the micro-channel 112. The micro-channel 110 is in fluid communication with the micro-channel 112 via the nano-channel 120. Therefore, if the reservoirs 106 and 108 are sufficiently filled with liquids that reach the micro-channels 110 and 112 and also the nano-channel 120, a liquid communication link can be established through the nano-channel 120.

Figure 3:
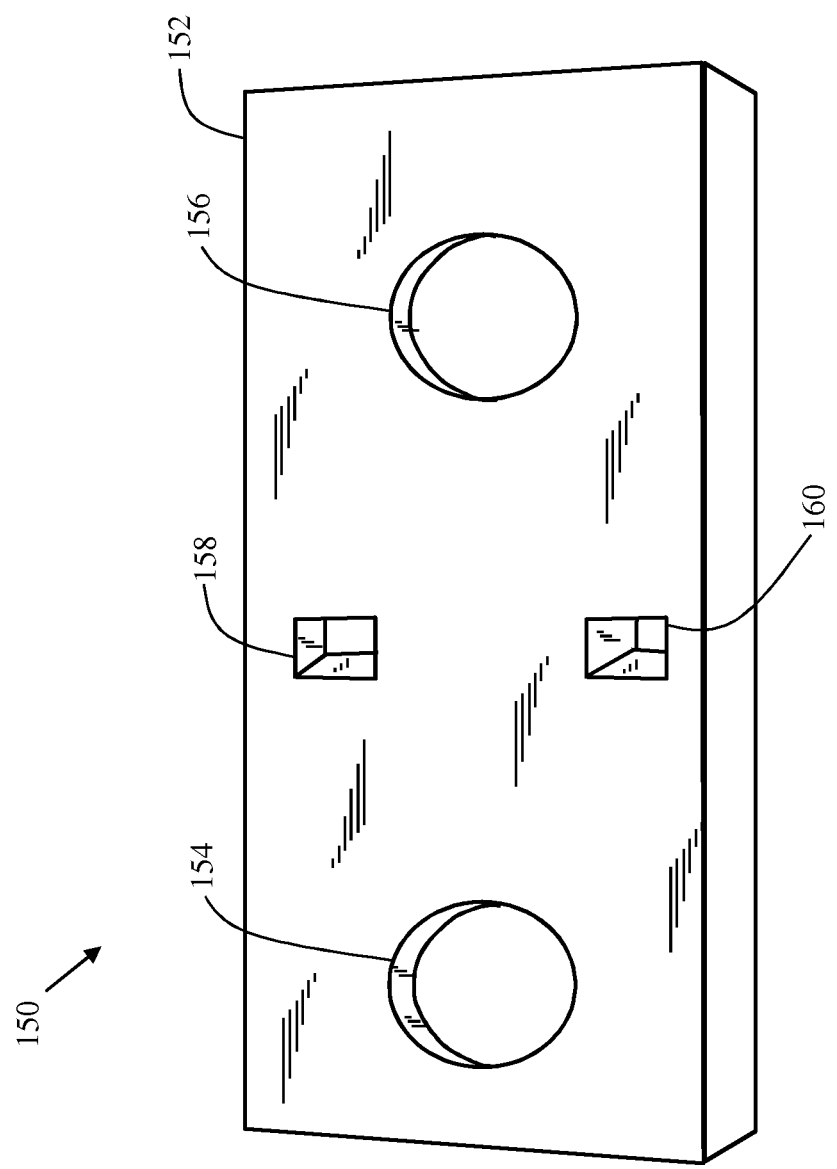
FIG. 3 depicts a perspective view of an access cover assembly of the nano-channel sensor assembly of FIG. 1.
Figure 4:
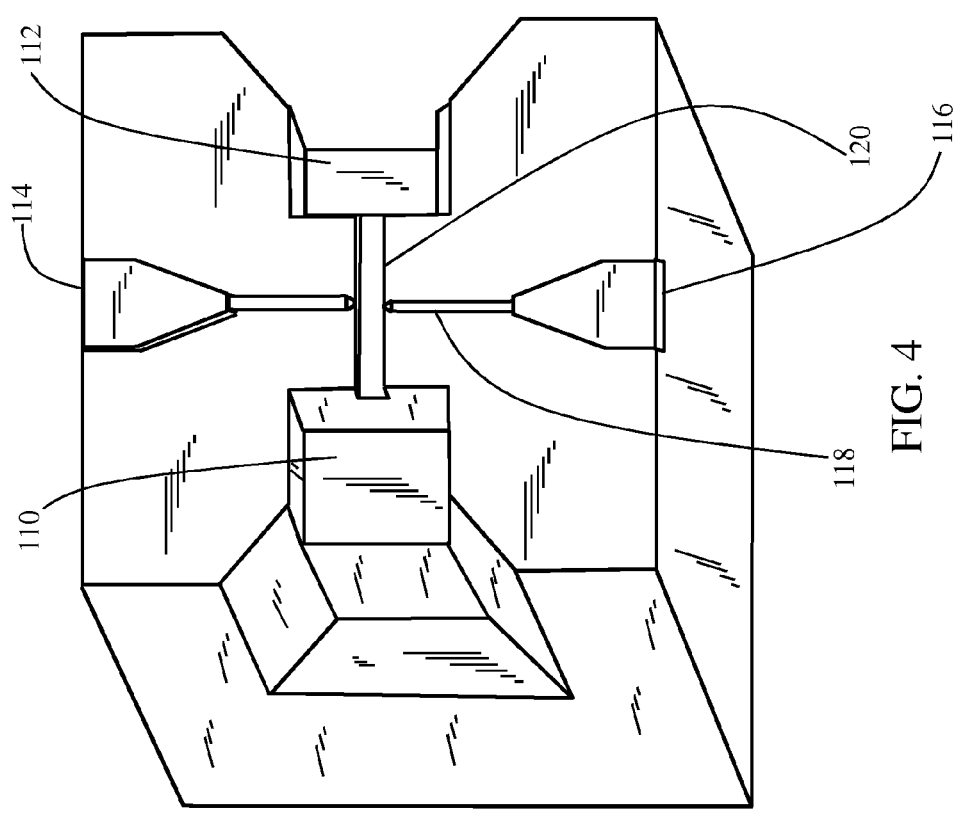
FIG. 4 depicts a fragmentary perspective view of a portion of the nano-channel sensor of FIG. 2, without a thermal oxide layer for clarity of depiction.

FIG. 3 depicts the access cover assembly 150. The access cover assembly 150 includes a lid 152 and access holes 154, 156, 158, and 160. In the exemplary embodiment depicted in FIG. 3, the lid 152 is made of Borosilicate glass, e.g., Pyrex® 7740 glass. The access holes 154, 156, 158, and 160 are formed in the lid 152 by drilling or other methods of forming holes in glass known in the art. The access holes 154 and 156 facilitate a liquid-tight interface for introduction of liquids into the reservoirs 106 and 108, as well as provide access to the biasing terminals 122 and 124. The access holes 158 and 160 allow access to conductor pads 114 and 116, respectively. Therefore, wires (not shown) can be threaded through the access holes 154, 156 to respective circuits of the stimulus/response circuit 20 for providing an appropriate biasing voltage to the biasing terminals 122 and 124 for biasing the liquid in the reservoirs 106 and 108, as described in greater detail below. Similarly, wires (not shown) can be threaded through the access holes 158, 160 to respective circuits of the stimulus/response circuit 20 for providing an electrical stimulus to the conductor pads 114 and 116 and for measuring the result of the stimulus at the conductor pads 114 and 116. The wires are connected to the biasing terminals 122 and 124 and to conductor pads 114 and 116. In addition to electrical accessibility, because the access cover assembly 150 is made of translucent glass, optical access is also provided to the entire nano-channel sensor 100.

The access cover assembly 150 is configured to fit over the nano-channel sensor 100. It will be appreciated that some compression (flattening) of the conductor pads 114 and 116 and of the electrode wire 118 may occur to ensure a tight fit between the access cover assembly 150 and the nano-channel sensor 100. The conductor pads 114 and 116 and the electrode wire 118 compress (flatten) when the access cover assembly 150 is placed over the nano-channel sensor 100 and further bonds to the thermal oxide layer 104. The compression (flattening) occurs because these structures (114/116 and 118) are made of soft material when placed in compression. Therefore, when assembled the access cover assembly 150 provides a surface against the nano-channel 120 that restricts the flow of liquid and any particles therein to be through the nano-channel 120 and not through a gap between the nano-channel sensor 100 and the access cover assembly 150.

Alternatively, the conductor pads 114 and 116 can be sized to be flush with the top surface of the thermal oxide layer 104. In this alternative embodiment, the electrode wire 118 can be recessed in the thermal oxide layer 104 so that placement of the access cover assembly 150 on the nano-channel sensor 100 results in a completely flush interface without dependence on compression (flattening) of the conductor pads 114 and 116 and the electrode wire 118.

The biasing terminals 122 and 124 provide the capability to charge the liquids in the reservoirs 106 and 108 to different voltages. The electrical potential difference between the liquids in the reservoirs 106 and 108 can lead to a pumping action between the reservoirs 106 and 108, through the micro-channels 110 and 112, and through the nano-channel 120.

While a two-piece embodiment is disclosed hereinabove, i.e., the nano-channel sensor 100 and the access cover assembly 150, a one-piece embodiment is also possible. In this alternative embodiment, the reservoirs, the micro-channels, the conductor pads, the electrode wire, the biasing terminals, and the nano-channels can all be fabricated within a substrate using etching and metallization processes followed by photoresist patterning and deposition/growth processes known in the art. Wire bonds can provide electrical access to the conductor pads and to the biasing terminals. Access holes can provide access to the reservoirs for introduction of samples as well as electrical/optical access to the biasing terminal, conductor pads, and reservoirs 106 and 108.

In operation, wires (not shown) are connected to the conductor pads 114 and 116 and to the biasing terminals 122 and 124. These wires are threaded through the access holes 154, 156, 158, and 160. The access cover assembly 150 is placed over the nano-channel sensor 100 and bonded to the thermal oxide layer 104 of the nano-channel sensor 100 to make the nano-channel sensor assembly 50.

Once assembled, the assembly 50 is calibrated by measuring the resistance across the nano-channel 120 under a plurality of conditions. In general, the calibration process includes applying a small biasing current to the conductor pad 114, and measuring the voltage difference between the conductor pads 114 and 116. The resistance is the ratio of the voltage difference between the conductor pads 114 and 116 and the current that is applied to the conductor pad 114.

A first calibration measurement involves measuring the resistance of the nano-channel 120 when the nano-channel is dry. This resistance constitutes an open circuit resistance. Next, both reservoirs 106 and 108 are filled with deionized (DI) water. The same procedure as described above is repeated to determine the resistance through the nano-channel 120 with DI water in the nano-channel 120. In order to overcome any capillary forces that may resist flow of the DI water through the nano-channel 120, the DI water can be pumped through the access hole 154 and forcibly taken out from the access hole 156.

By contrast, other liquids with ions can also be used to test the transfer of liquids through the nano-channel 120. In order to assist the transfer of these ionized liquids through the nano-channel 120, an alternative method can be used to pump the liquid from one reservoir to the other reservoir. For example, the sample liquids in the reservoirs 106 and 108 can be charged to different potentials by applying different voltages to the biasing terminals 122 and 124 to form an electrophoretic pump, known in the art.

Next a biological sample containing nano-sized particles is introduced to the reservoir 106 through the access hole 154. By monitoring the resistance across the nano-channel 120, and comparing the resistance to the open circuit and DI resistances, presence of particles and the size of particles can be ascertained. It should be appreciated that the sensor stimulus/response circuit 20, depicted in FIG. 1, provides the necessary stimuli for measuring the resistance across the nano-channel to the nano-channel sensor 100 (conductor pads 114 and 116) and communicates the effect of the stimuli to the processing circuit 14.

While the stimuli applied by the stimulus/response circuit 20, as described above, may seem to be of the direct current (DC) type, no such limitation should be attributed to the stimulus/response circuit 20. FIG. 5A depicts an exemplary electrode wire structure 180 that is used with microwave measurements for measuring conductance and admittance. Three sets of electrode wires $118_a$, $118_b$, and $118_c$ are connected to respective conductor pads ($114_a$, $114_b$, and $114_c$ and $116_a$, $116_b$, and $116_c$). Each electrode wire of each set may be connected to a respective conductor pad, or alternatively one conductor pad may be connected to more than one electrode wire. In general, the conductor pads 114 and 116 of the disclosed nano-channel sensor 100 (FIG. 2 and FIG. 5A) are configured such that the nano-channel measuring system 10 can measure bio-molecules and other particles within the nano-channel 120 with microwave signals.

FIG. 5B depicts an electrical model of the conductor pads 114 and 116, the electrode wire $118_i$, i.e., $118_a$, $118_b$, and $118_c$, and the nano-channel 120 of FIG. 5A from a microwave stimulus aspect. The electrical model includes a first capacitance 182, a resistance 184, and a second capacitance 186. The aforementioned components of FIG. 5B are connected in series. The first capacitance and the second capacitance 182 and 186 generate a frequency-dependent impedance across the nano-channel 120. The conductor pads 114 and 116, the electrode wire $118_i$, and the nano-channel 120 are configured such that these structures provide a constant characteristic impedance, e.g., 50Ω, or a larger impedance, e.g., 1 kΩ at a target microwave transmission. The constant impedance design eliminates undesired reflections bouncing off from discontinuities in both conductor pads 114 and 116 and the electrode wire 118 that can form a standing wave and thereby disturbing detected signals. Furthermore, measurements under a high impedance environment, such as 1 kΩ characteristic impedance, may also provide less parasitic reflection from the high-impedance nano-channel 120. It should be appreciated that as in the case of high impedance designs, precautions such as radiation proof features of high impedance lines should be practiced to lessen parasitic reflections and cross talk between signals. Also, established calibration techniques known in the art is used to remove parasitic effects of conductor pads 114 and 116 and biasing terminals 122 and 124 and the fluidic media in the nano-channel 120.

The detection of bio-molecules or other nano-particles flowing inside the nano-channel is accomplished by either measuring the transmittance or reflectance of stimuli signals generated by the stimulus/response circuit 20. Part of the stimulus/response circuit 20 is constructed with a network analyzer configured to analyze microwave stimuli which can provide advantages over DC conductance measurements, described above. The microwave measurements are performed using microwave S-parameters which are based on both conductance and capacitance of the measured section of the nano-channel 120. As a result, a clearer picture of the disturbances in charge transfer through the nano-channel 120 and dielectric properties of the liquid therein as the bio-molecules or nano-particles traverse across the nano-channel 120 is obtained. Furthermore, the microwave measurements are performed across a range of frequencies. Not only the effect of flicker noise at low frequencies can be completely masked, i.e., filtered, but also more data about conductivity and dielectric properties of the biomolecule or other particles inside the nano-channel 120 is obtained from higher frequencies which increases the accuracy and sensitivity of the measurements.

Calibration can be performed to remove the effects of parasitic conductance and admittance of the section of the nano-channel 120 under examination and thus focus on the disturbances in the media as bio-molecules or nano-particles flow through the nano-channel 120. While a simple method of averaging DC signals in conductance measurements is straightforward, the slow nature of this approach prohibits the system from operating at medium to high flow rates. On the other hand microwave measurements with a few frequency points can be used in very short periods of time with each measurement repeated and averaged for enhanced accuracy. Also, not only does a microwave measurement provide information about both conductivity and dielectric properties of bio-molecules, the microwave measurement is less sensitive to the gap between the molecule and the spacing between the sections of the electrode wire $118_i$, as well as the rotation of bio-molecules inside the nano-channel 120. The reduced sensitivity is mainly because the gap between the molecule and the sections of the electrode wire $118_i$ and the rotation of bio-molecules only affect conductivity. However, admittance which is a function of the dielectric property of the molecule remains unaffected.

FIGS. 6 through 11 depict steps in fabricating the nano-channel sensor 100. The steps depicted in these figures can be performed by integrated circuit fabrication processes that are known in the art. FIG. 6 depicts the substrate 102. The substrate 102 can be the starting point for a wafer which will include multiple nano-channel sensors 100. Individual nano-channel sensors 100 can later be diced and singulated from the wafer. Examples of a suitable substrate material for the substrate 102 are silicon, glass, germanium, silicon carbide, Galium Arsenide, Indium Phosphide, and silicon germanium.

FIG. 7 depicts the substrate 102 after formation of cavities 206 and 208 that will be used to generate reservoirs 106 and 108; and after formation of cavities 210 and 212 that will be used to generate micro-channels 110 and 112. The cavities 206, 208, 210, and 212 are formed using a two-step dry etch process, e.g., deep reactive ion etching (known in the art as DRIE) in a high resistivity substrate material, e.g., silicon. The cavities 206 and 208 are larger and deeper (about 150 μm deep), while the cavities 210 and 212 are shallower (about 1 μm deep). The cavities 210 and 212 are adjacent to the cavities 206 and 212, respectively.

Due to limitation of lithography in stepping from the electrode wire 118 to the micro-channels 110 and 112, the depth of micro-channels 110 and 112 is limited. Otherwise, too deep of micro-channels prevent adequate photoresist step coverage. The reservoir/micro-channel formation process was performed by etching the shallower cavities 210 and 212 first, using the DRIE process, followed by covering the cavities 210 and 212 by a photoresist droplet, and continuing the DRIE process until the deeper cavities 206 and 208 (150 μm) are formed.

FIG. 8 depicts the substrate after formation of a thermal oxide layer 104 over the cavities 206, 208, 210, and 212. The thermal oxide layer 104 is formed (e.g., deposited) onto the substrate 102 and cavities 206, 208, 210, and 212 in order to electrically isolate the substrate 102 from other structures (as discussed above). Examples of suitable material for the thermal oxide layer 104 are silicon oxides, and silicon nitrides, i.e., for the silicon substrate. Examples of methods of deposition are thermal growth (for silicon oxides), chemical vapor deposition, and physical vapor deposition. The thermal oxide layer 104 is formed over the entire span of substrate 102. The thermal oxide layer 104 has a thickness of about 7000 Å, i.e., 0.7 μm. Formation of the thermal oxide layer 104 on the substrate 102 and cavities 206, 208, 210, and 212, results in the formation of the reservoirs 106, 108 and the micro-channels 110 and 112.

FIG. 9 depicts an intermediate state of the nano-channel sensor 100 after an etching process that forms recesses 250 where the conductor pads 114 and 116 are to be formed. An example of the etching process is a reactive ion etching process after photoresist patterning the area to be etched. A depth of about 100 nm is etched by the exemplary etching process into the thermal oxide layer 140.

FIG. 10 depicts an intermediate state of the nano-channel sensor 100 after formation of the conductor pads 114 and 116. Layers of material 252 for forming the conductor pads 114 and 116 is deposited on top of the recessed thermal oxide layer 104. Examples of methods of deposition are chemical vapor deposition and physical vapor deposition. The layers of material 252 can alternatively be grown by an epitaxial growing process, or by a metal sputtering operation. For improved bonding to the thermal oxide layer 104, a layer of about 10 nm of chromium (Cr) is first formed, followed by forming a layer of about 100 nm of gold (Au). Other examples of material of the layers 252 are doped polysilicon, silver, copper, titanium, platinum, tungsten, aluminum, iridium, ruthenium, and titanium nitride.

FIG. 11 depicts an intermediate state of the nano-channel sensor 100 after formation of the electrode wire 118. The electrode wire 118 is formed by using a high resolution focused ion beam, known in the art as a FIB. An FEI Nova 200 was used to perform a FIB-assisted deposition of a layer 254 to form the electrode wire 118. It is possible to place an electrode wire as thin as 1 nm using this process. In the exemplary embodiment, an electrode wire 118 of about 40 nm width and about 10 nm depth of platinum material was formed which connects the two conductor pads 114 and 116. Alternatively, an electron beam nanolithography process, followed by a tilted metal sputtering process, both of which are known in the art, can also be used to form the electrode wire 118.

Once the electrode wire 118 is formed, the FIB is used to cut a 50 nm wide and a 20 nm deep nano-channel crossing and therefore cutting the electrode wire 118. The FIB process etches metals much faster than the thermal oxide layer 104. Therefore, removing the platinum wire and its underlying thermal oxide layer 104 can be performed in one single pass.

Figure 12:
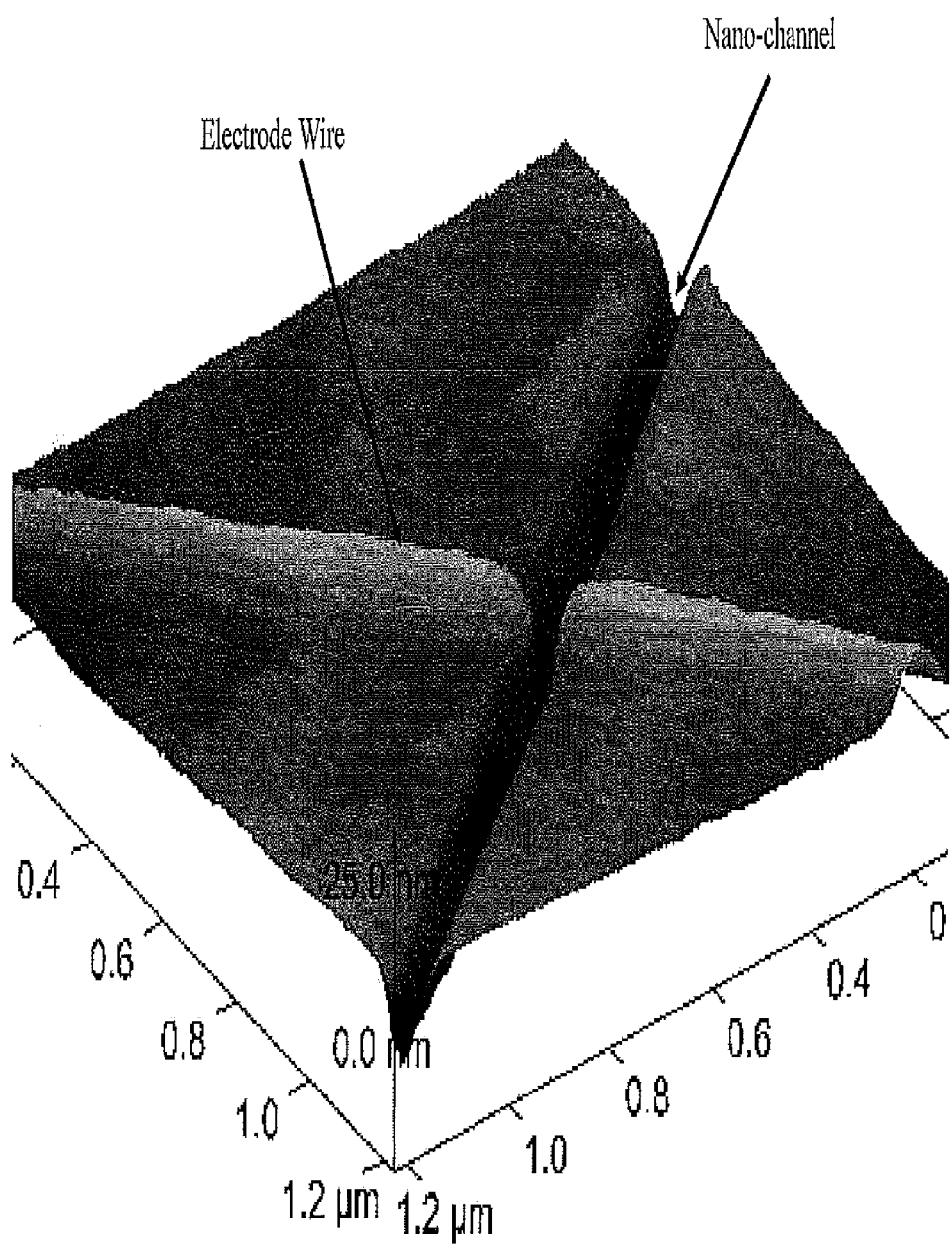
FIG. 12 depicts an atomic force microscope (AFM) image of a focus ion beam fabricated nano-channel and an electrode wire.

FIG. 12 depicts an atomic force microscope (AFM) image of the FIB fabricated nano-channel 120 (50 nm wide and 20 nm deep), labeled in FIG. 12 as nano-channel, and the electrode wire 118, labeled in FIG. 12 as electrode wire. FIG. 12 clearly depicts no blockage in the nano-channel 120 at the location where the electrode 118 wire was cut.

While a FIB process is described above to etch away the thermal oxide and the platinum wire to form the nano-channel 120, AFM can also be used to form the nano-channel 120. The AFM technology can now provide high resolution scratching of a surface in the single-digit nm range (down to 1-2 nm). Another alternative approach for forming the nano-channel 120 is by using an electron beam lithography followed by an anisotropic DRIE process, both of which are known in the art.

Figure 13:
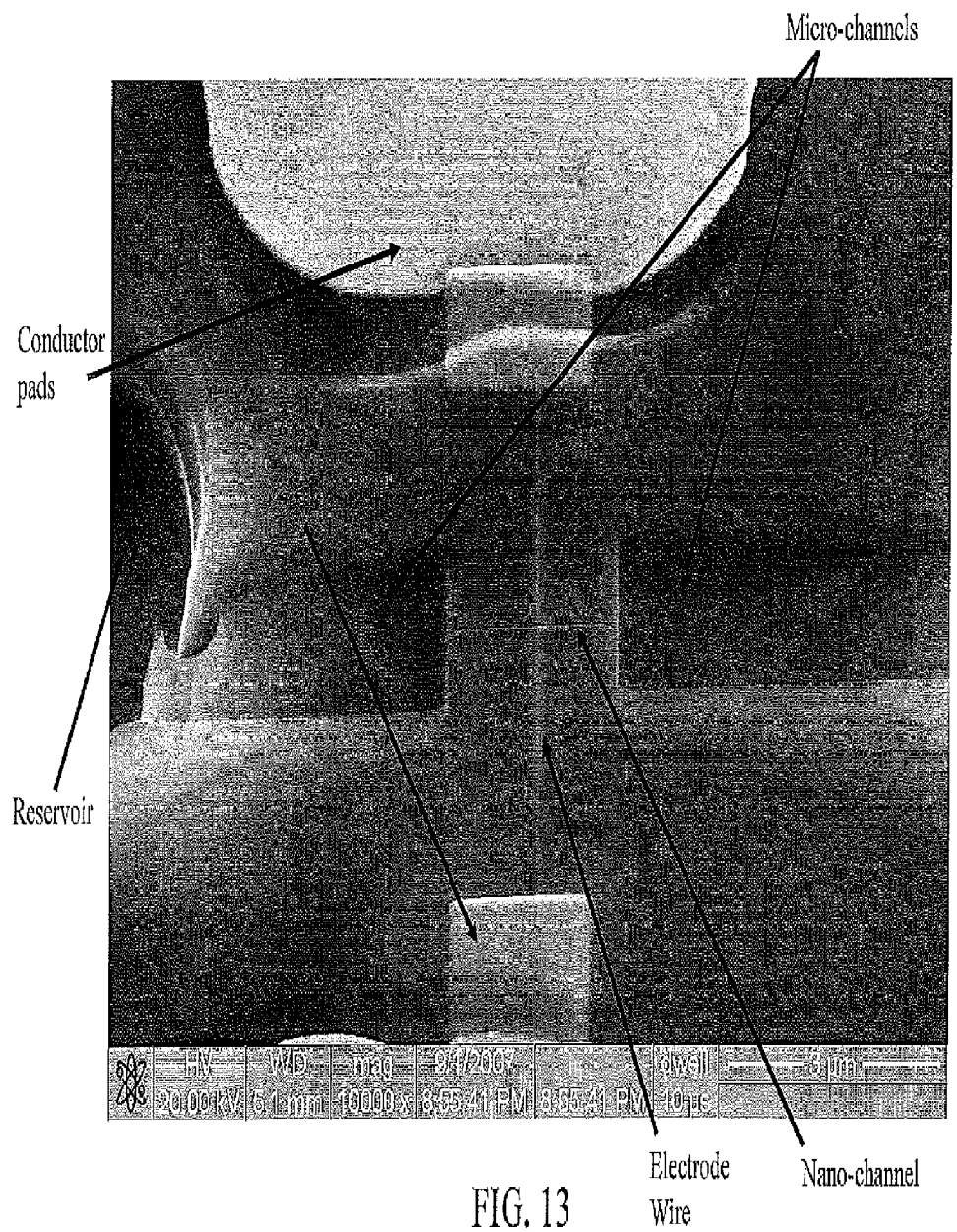
FIG. 13 depicts a scanning electron microscope image of the nano-channel, the electrode wire, conductor pads, and micro-channels of the nano-channel sensor of the current disclosure.

FIG. 13 depicts a scanning electron microscope image of the nano-channel 120 (labeled in the figure as nano-channel), electrode wire 118 (labeled in the figure as electrode wire), conductor pads 114 and 116 (labeled in the figure as conductor pads), and micro-channels 110 and 112 (labeled in the figure as micro-channels). FIG. 13 clearly depicts the relationship between the micro-channel 110 and the reservoir 106 (labeled in the figure as reservoir).

Once the nano-channel sensor 100 is fabricated, access holes 154 and 156 of 3 mm in diameter each are drilled in the lid 152 (7740 glass wafer) of the access cover assembly 150, as well as access holes 158 and 160. The access cover assembly 150 is then bonded to the nano-channel sensor 100 using anodic bonding techniques known in the art. An oxygen plasma surface activation process was used to facilitate the wetting of the nano-channel 120 prior to bonding the access cover assembly 150 to the nano-channel sensor 100.

The nano-channel sensor 100 was washed by way of the following steps. The nano-channel sensor 100 was soaked in acetone, methanol, isopropanol alcohol (IPA) and DI water in a vacuum chamber (each soaking step was about 30 minutes long). To replace acetone with DI water presents a challenge due to their mutual immiscibility. Flushing the nano-channel 120 with methanol and IPA prior to DI water solves the above mentioned challenge. Following the wetting steps, access holes 154 and 156 were connected to a pump and DI water was pumped through. The pumping was performed using two syringe pumps, one connected to the access hole 154 for pushing the liquid while the second one was connected to the access hole 156 to provide a suction thereby generating a high pressure gradient across the nano-channel 120.

Figure 14:
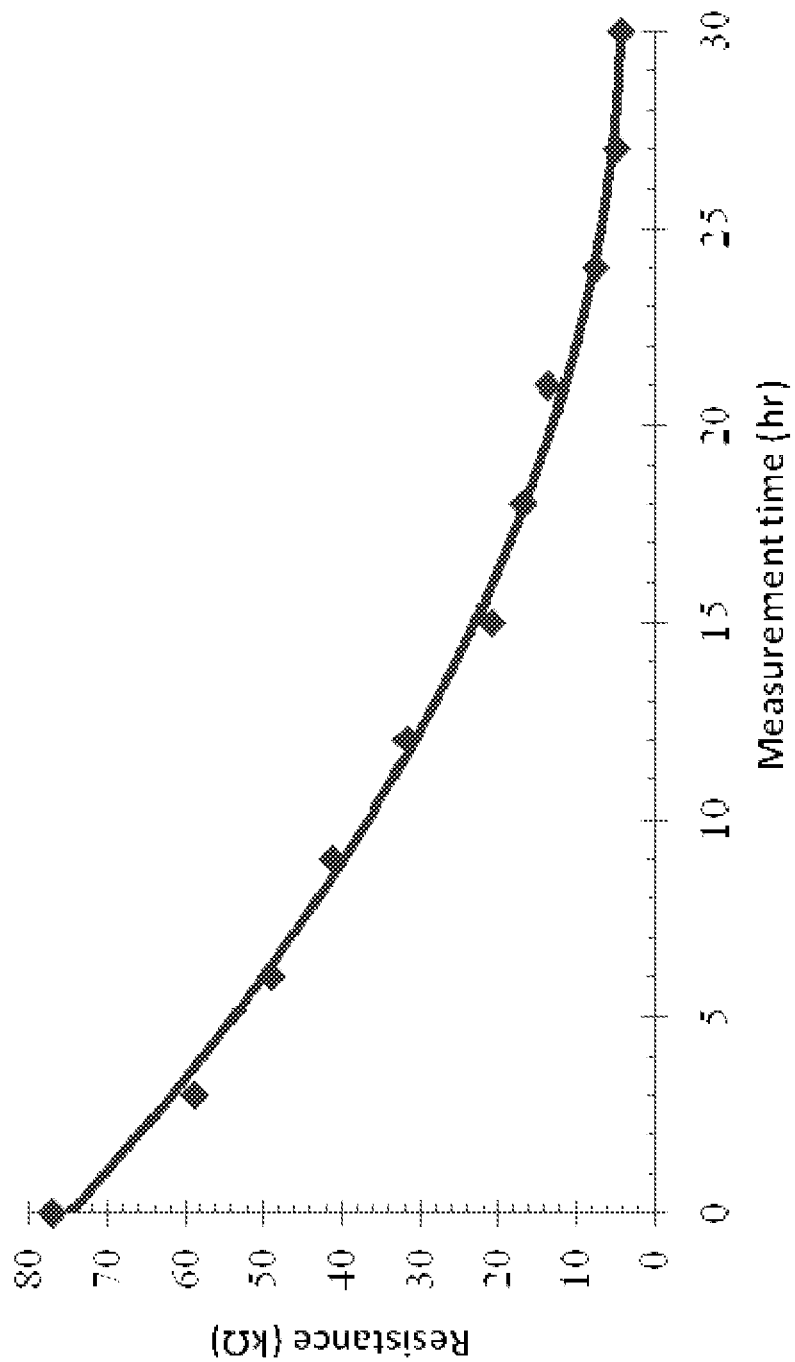
FIG. 14 depicts a graph of resistivity vs. time of deionized water passing through the nano-channel at 1 kHz excitation of the electrode wire.

In order to verify the functionality of the nano-channel 120, a resistivity measurement was performed. FIG. 14 depicts a graph of resistivity vs. time of the DI water passing through the nano-channel 120 at 1 kHz excitation of the electrode wire 118. The resistivity measurement was performed by placing DI water in the reservoir 108 and micro-channel 112 and pumping 0.1 molar phosphate buffered saline PBS from the access hole 154 to the reservoir 106 for two days. The DI water resistivity drops as more PBS is pumped through the channel, thus verifying the intended functionality of the nano-channel 120. Next, negatively charged FluoSpheres® carboxylate-modified nanospheres (20 nm nominal diameter, Invitrogen) were electrophoretically pumped through the nano-channel. For this test, the nano-channel 120, the micro-channels 110 and 112, and the reservoirs 106 and 108 were filled with 0.1 molar PBS. Then the FluoSpheres® were introduced into the grounded reservoir 106 while the reservoir 108 was connected to a positive voltage (10V) thus forcing the negatively charged particles toward the reservoir 108.

Figure 15:
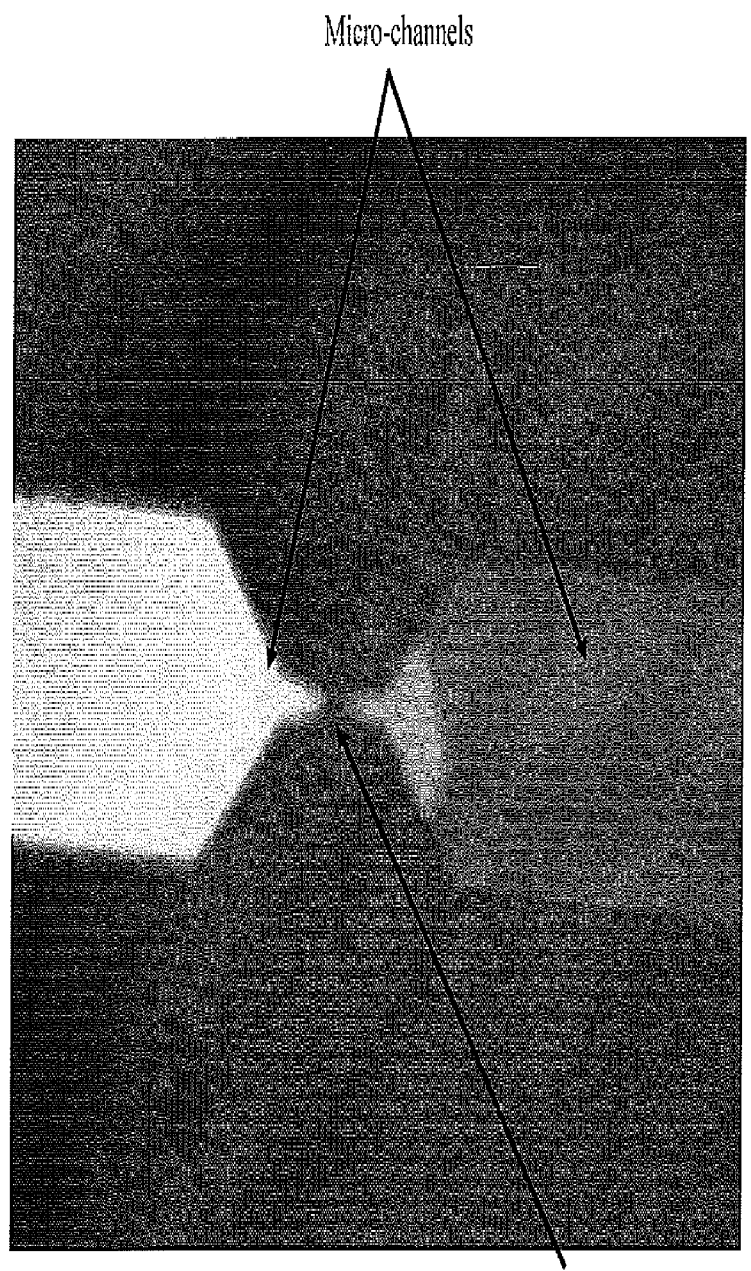
FIG. 15 depicts a fluorescence image of the nano-channel of the nano-channel sensor of FIG. 2.

FIG. 15 depicts a fluorescence image of the nano-channel 120 (labeled in the figure as nano-channel) of the nano-channel sensor 100 clearly showing the movement of the fluorescence particles from the micro-channel 110 (bright side) to the micro-channel 112 (labeled in the figure as micro-channels) through the nano-channel 120.

Figure 16:
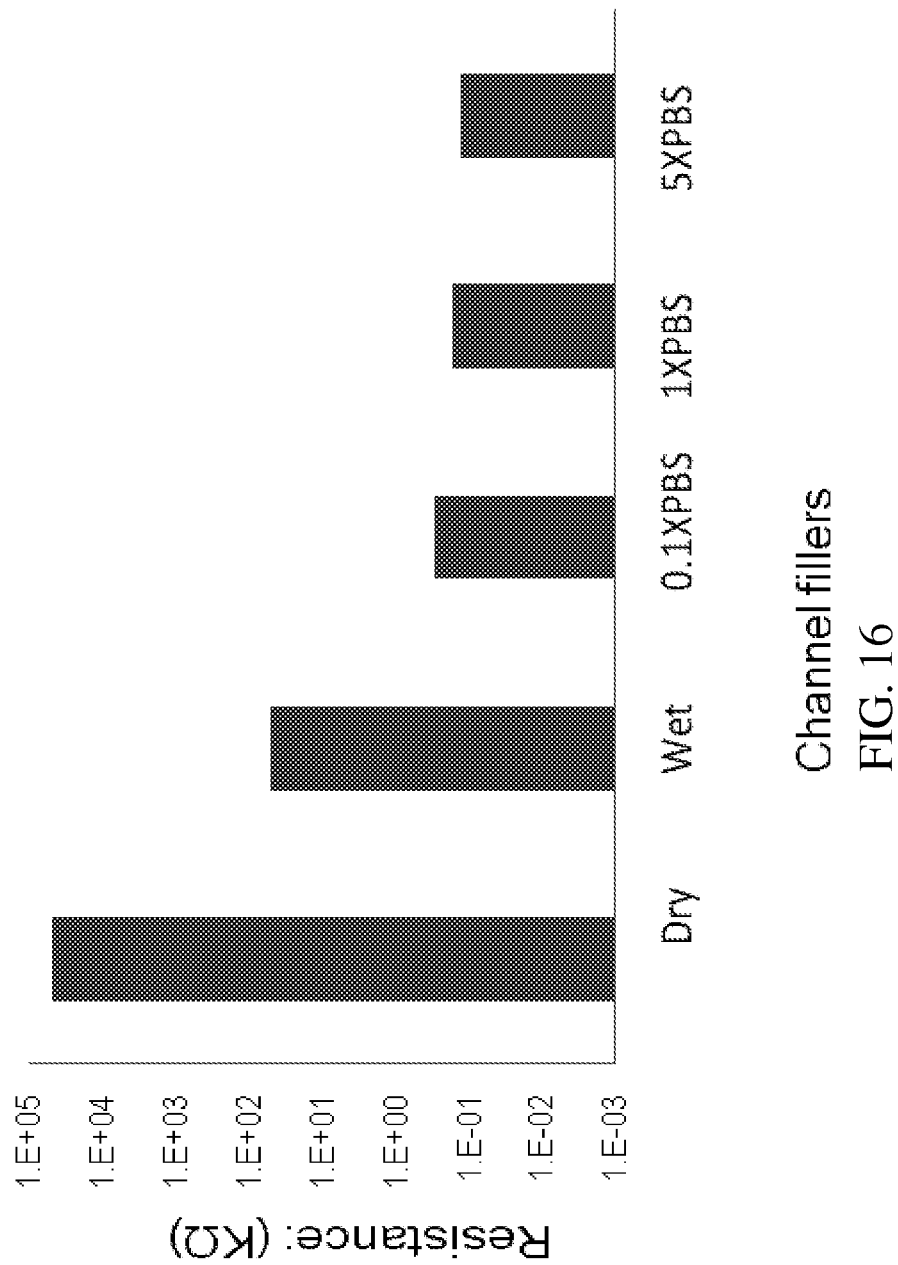
FIG. 16 depicts resistance measurement of the nano-channel at different conditions.

Another resistivity measurement was also performed at different conditions, described below. FIG. 16 depicts resistance measurement of the nano-channel 120 at these different conditions. PBS solutions of various concentrations were introduced into the nano-channel sensor 100 and the resistivity of each was measured. The resistance measurements were carried out while the nano-channel 210 was dry (prior to introduction of a PBS solution), i.e., an open circuit, then wetted with DI water, and then filled by different concentrations of PBS solutions. With the nano-channel dry, the resistance was high ($5 \times 10^7 \Omega$), as to be expected. The high resistance indicates proper cutting of the electrode wire 118 during the FIB process or the AFM scratching process. With DI water, the resistance dropped to $5 \times 10^4 \Omega$, indicating presence of the DI water in the nano-channel 120. Thereafter, the resistance decreased uniformly as more concentrated PBS solutions were introduced into the reservoir 106, clearly demonstrating the intended functionality of the nano-channel 120 and the electrode wire 118.

While the aforementioned embodiment of the nano-channel measuring system 10 is directed to measuring resistivity, impedance, and admittance of the medium passing through the nano-channel 120, it should be appreciated that the embodiments described above can also be used for manipulating biomaterials with nano-size features. For example, Deoxyribonucleic acid (DNA) molecules and Ribonucleic acid (RNA) molecules are made of strands that include nano-size features. The embodiments described above can be used to sequence the DNA and RNA strands. The size of the electrode wire 118 (or $118_a$, $118_b$, and $118_c$ in case of FIGS. 5A and 5B) and the nano-channel 120 can be configured to identify sections of the DNA and RNA strands as these sections flow by the electrode wire 118. The DNA and RNA strands are suspended in a liquid which is electrophoretically pumped (or alternatively, mechanically pumped by establishing a liquid tight interface with the access holes 154 and 156), as described above, to facilitate the transfer of the strands through the nano-channel 120.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A method for forming a nanofluidic channel measuring system, comprising:
    forming a first trench in a substrate;
    forming a second trench in the substrate, the first trench and the second trench are separated by a first width;
    providing a first conductor pad at a first location;
    providing a second conductor pad at a second location;
    forming a first nano-wire for coupling the first conductor pad with the second conductor pad;
    forming a first shallow trench between the first trench and the second trench adjacent to a first reservoir;
    forming a second shallow trench between the first trench and the second trench adjacent to a second reservoir;
    providing a third conductor pad;
    forming a second nano-wire between the first conductor pad and the third conductor pad; and
    forming a nano-channel through the first nano-wire, the nano-channel also coupling the first trench and the second trench, the nano-channel configured to sever the first nano-wire and the second nano-wire, wherein the nano-channel is substantially perpendicular to the second nano-wire.

2. The method of claim 1, wherein the first nano-wire extends over the first width.

3. The method of claim 2, wherein the nano-channel extends along the first width.

4. The method of claim 3, wherein the nano-wire is substantially perpendicular to the nano-channel.

5. The method of claim 1, further comprising:
    providing a thermal oxide layer over the substrate prior to providing the first conductor pad and the second conductor pad forming a first recess at the first location where the first conductor pad is to be provided; and
    forming a second recess at the second location where the second conductor pad is to be provided, wherein the first conductor pad is provided inside the first recess and the second conductor pad is provided inside the second recess.

6. The method of claim 5, wherein the first conductor pad and the second conductor pad are thicker than depths of the first recess and the second recess.

7. The method of claim 1, wherein the first trench and the second trench are formed by deep reactive ion etching, and the first nano-wire is formed by a first focus ion beam process.

8. The method of claim 7, wherein the nano-channel is formed by a second focused ion beam process.

9. The method of claim 7, wherein the nano-channel is formed by an atomic force microscope.

10. The method of claim 1, wherein the first shallow trench and the second shallow trench are formed by a deep reactive ion etching process.

11. The method of claim 1, further comprising:
    forming a layer to be placed over the substrate;
    forming access holes to provide access to the first trench and the second trench;
    forming access holes to provide access to the first conductor pad and to the second conductor pad; and
    bonding the layer over the substrate.

12. The method of claim 1, further comprising:
    applying a microwave stimulus to the first conductor pad;
    measuring conductance across the nano-channel by sensing a response at the second conductor pad; and
    measuring reflectance of the microwave stimulus by sensing a response at the first conductor pad.

13. The method of claim 1, further comprising:
    storing command instructions in a memory; and
    configuring a processor to execute the command instructions to
        energize the first conductor pad,
        measure voltage at the second conductor pad, and
        provide an output associated with electrical characteristics between the first conductor pad and the second conductor pad, wherein the electrical characteristics include impedance between the first conductor pad and the second conductor pad, and admittance between the first conductor pad and the second conductor pad.

14. A nanofluidic channel measuring system, comprising:
a substrate having a first trench formed therein and a second trench formed therein, the first trench and the second trench are separated by a first width;
a first conductor pad disposed at a first location;
a second conductor disposed at a second location;
a nano-channel configured to couple the first trench and the second trench along the first width;
a first nano-wire section extending form the first conductor pad to the nano-channel; and a second nano-wire section extending from the second conductor pad to the nano-channel;
a first shallow trench disposed between the first trench and the second trench adjacent to a first reservoir;
a second shallow trench disposed between the first trench and the second trench adjacent to a second reservoir;
a third conductor pad disposed at a third location; and
the second nano-wire configured to be between the first conductor pad and the third conductor pad, wherein the nano-channel severs the second nano-wire, and the nano-channel is substantially perpendicular to the second nano-wire.

15. The nanofluidic channel measuring system of claim 14, further comprising:
a thermal oxide layer disposed over the substrate, wherein the thermal oxide layer is disposed between the substrate and the first conductor pad and between the substrate and the second conductor pad;
a first recess having a first depth in the thermal oxide disposed at the first location under the first conductor pad; and
a second recess having second depth in the thermal oxide disposed at the second location under the second conductor pad.

16. The nanofluidic channel measuring system of claim 15, wherein the first conductor pad is thicker than the first depth of the first recess and the second conductor pad is thicker than the second depth of the second recess.

17. The nanofluidic channel measuring system of claim 14, further comprising:
a layer disposed over the substrate;
access holes disposed in the layer to provide access to the first trench and the second trench; and
access holes disposed in the layer to provide access to the first conductor pad and to the second conductor pad.

18. The nanofluidic channel measuring system of claim 14, further comprising:
a memory for storing command instructions; and
a processor configured to execute the command instructions to
energize the first conductor pad,
measure voltage at the second conductor pad, and
provide an output associated with electrical characteristics between the first conductor pad and the second conductor pad, wherein the electrical characteristics include impedance between the first conductor pad and the second conductor pad, and capacitance between the first conductor pad and the second conductor pad.

* * * * *